United States Patent [19]

McCoy

[11] Patent Number: 5,453,277
[45] Date of Patent: Sep. 26, 1995

[54] METHOD OF CONTROLLING SOIL PESTS

[76] Inventor: Paul E. McCoy, 255 Dolphin Point Rd., Unit 511, Clearwater, Fla. 34630

[21] Appl. No.: 146,958

[22] Filed: Nov. 3, 1993

Related U.S. Application Data

[62] Division of Ser. No. 776, Jan. 5, 1993, abandoned.

[51] Int. Cl.⁶ .................................................. A01N 25/26
[52] U.S. Cl. ................................... 424/408; 424/409
[58] Field of Search ...................... 424/408, 410, 424/418, 692, 682; 514/23, 2, 24, 27, 64

[56] References Cited

U.S. PATENT DOCUMENTS

| | | | |
|---|---|---|---|
| Re. 32,909 | 4/1989 | Lionelle et al. | 556/131 |
| 3,567,460 | 3/1971 | McCoy | 426/635 |
| 4,589,906 | 5/1986 | Brunn et al. | 71/80 |
| 5,162,349 | 11/1992 | Beriger et al. | 514/363 |
| 5,187,185 | 2/1993 | Outcalt et al. | 514/408 |

*Primary Examiner*—Thurman K. Page
*Assistant Examiner*—Neil Levy
*Attorney, Agent, or Firm*—Herbert W. Larson

[57] ABSTRACT

Soil dispersible and water dispersible granular nutrients for use in a method of controlling soil pests include granules having a crystallized saccharide binder with a magnesium carboxylate of a nutrient embedded therein. Preferably magnesium carboxylate is applied to soil in a saccharide binder at the rate of about from 100 to 200 lbs. per acre to control soil pests such as nematodes and insects.

10 Claims, 1 Drawing Sheet

5,453,277

METHOD OF CONTROLLING SOIL PESTS

PRIOR APPLICATION

This application is a divisional OF application Ser. No. 08/000,776, filed Jan. 5, 1993, now abandoned.

BACKGROUND OF THE INVENTION

1. Field of The Invention

The present invention relates to a method of controlling soil pests by applying to soil a soil dispersible, granular nutrient. More particularly, the present invention relates to applying granules having carboxylate nutrients embedded within a saccharide binder to soil containing soil pests.

2. Description of the Prior Art

Numerous tests and many years of experience of the agriculture industry of the United States have demonstrated the need for certain nutrients for plant and animal growth. Some are more difficult than others to supply in a form which is easily taken up. In soil, there is the further problem of maintaining the nutrients in position over time.

U.S. Pat. No. 3,567,460 relates to the use of soil dispersible and water dispersible plant and animal nutrient compounds in a granular form comprising nutrient particles selected from the group made up of metallic oxides, metallic sulphates, metallic oxysulphates and metallic oxsulphates placed within a water-soluble saccharide binder.

U.S. Re. Pat. No. 32,909 relates to the use of metal oxycarboxylates as suppliers of metal nutrients to plants, animals and humans.

U.S. Pat. No. 4,589,906 relates to the use of various divalent and trivalent metals in organic carboxylate form as starting materials for the formulation of plant fertilizers.

Prior art nutrient compounds generally suffer from disadvantages in speed and effectiveness of uptake of the nutrients. Therefore, there is a need for granular nutrient products which make the nutrients in the granules more available for plant and animal uptake. It is an object of the present invention to provide such products and describe how soil pests can be controlled by such products.

SUMMARY OF THE INVENTION

Accordingly, the present invention is directed toward providing granular compounds for controlling soil pests. Compounds of the present invention are formed by agglomerating or otherwise binding the fines into a granule whose outer coating is a water soluble material. During the process of the agglomeration, the nutrient fines undergo a chemical reaction with the binder whereby carboxylated nutrients are produced as the end product. By utilizing the teachings of the invention, a certain amount of gas such as carbon dioxide is entrapped in the granule. When the outer coating dissolves in the presence of moisture, the expanding volume of the gas explodes the granule and aids in dispersing the carboxylated nutrients throughout the medium surrounding the original granule.

The materials employed in the methods of this invention are granules having a crystallized saccharide binder with carboxylates of a nutrient embedded therein. The granules are applied to soil containing pests such as nematodes and insects to control such pests. Application rates of from about 100 to 200 pounds per acre are employed in the methods of the invention.

Other features and advantages of the present invention will become apparent from the following description of the invention which refers to the accompanying drawings.

For the purpose of illustrating the invention, there is shown in the drawings an embodiment which is presently preferred; it being understood, however, that the invention is not limited to the precise arrangements and instrumentalities shown.

DETAILED DESCRIPTION OF THE INVENTION

Figure 1:
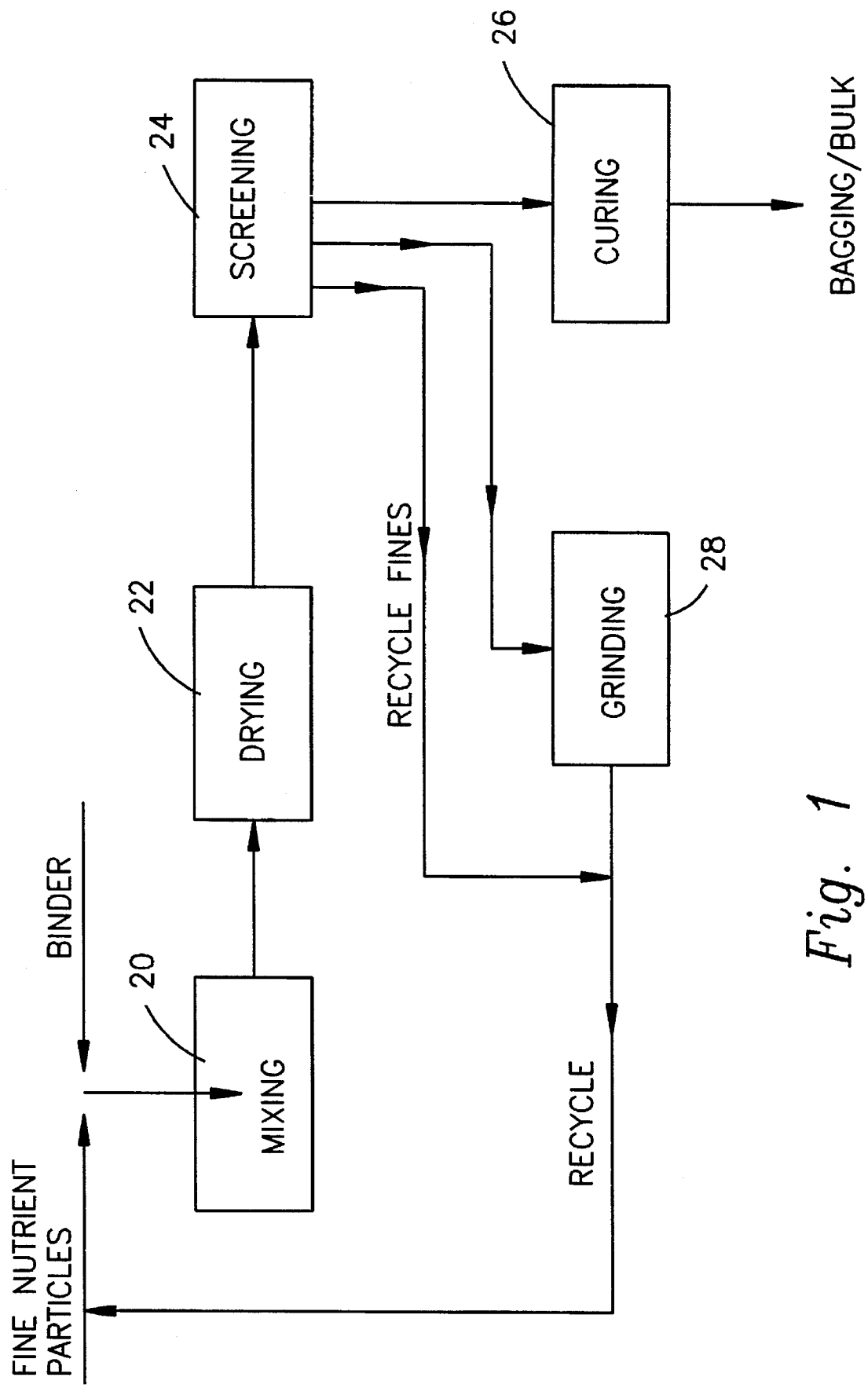
FIG. 1 is a schematic drawing showing the process steps of one preferred manufacturing process in accordance with the invention.

Preferred compounds which may be provided in accordance with the invention include major primary nutrients without which life cannot be sustained (e.g., phosphate and potassium) and secondary nutrients required in some quantities for growth and nutrients which, even if not necessary to sustain life, will further improve plant and/or animal growth and health. These nutrients are well known in the art. Among the nutrients which may be supplied in accordance with the invention are cationic nutrients such as manganese, zinc, copper, iron, calcium, potassium, magnesium, boron, cobalt, molybdenum, lithium, yttrium, thorium and rare earth elements. Cationic metals are especially useful in accordance with the invention.

The invention utilizes, as starting compounds, a reactant binder and reducible compounds which include desired nutrients in the form of oxides, sulfates and other reducible compounds and salts. The reducible compounds are reduced in the presence of reducing sugars in the binder, (i.e., monosaccharides and aldehyde-functional disaccharides) and form carboxylates of said nutrient. For example, when a cationic metal nutrient compound such as a metal oxide is reacted with reducing sugars, the desired metal carboxylate products are formed in an exothermic reaction. A stoichiometric excess of reducing sugars is preferred because it is desirable to create as much carboxylate product as possible while leaving behind only a small amount of unreacted reducible nutrient compounds. Preferably the ratio of product carboxylate to unreacted starting nutrient compounds should be at least 1:1, preferably 3:1 and more preferably, in excess of 9:1. It is believed that the uptake of product carboxylate is greatly improved relative to the starting compounds such as metal oxides.

Suitable starting compounds include, but are not limited to various oxides of manganese, zinc, copper, iron and magnesium (e.g., MnO, $Fe_2O_3$ and FeO). Mixtures of the compounds may also be used, for example, mixtures of iron and manganese compounds in a ratio between about 1.5:1 and 2.0:1 by weight.

The reducible starting compounds are preferably formulated as fine particles (e.g., about 44 microns or smaller) and are introduced into a mixer as a powder countercurrent to a spray of the binder which crosses the stream of reducible starting compound allowing the binder and starting compounds to meet. The binder provides the reducing sugars which react with the starting compounds to form carboxylates, and also provides the saccharides which preferably form a crystalline shell about the carboxylates that are formed.

The starting materials and binder, after making contact, fall into a mixer. A mixer which can be utilized, for example, is a drum open at one end having a diameter of about 48 inches and an interior length of about 30 inches. The drum is angled so that its open end is above its closed end, and the drum is rotated about its cylindrical axis. As the drum is rotated, granules of the binder are formed having embedded therein a combination of starting compounds and product carboxylates. It should be noted that some of each is expected because the conversion of starting material to carboxylate begins at initial contact but is not completed until a later curing step described below.

The granules grow in size as additional binder is continually coated about the outer surface of the granule in the mixer. Time in the mixer preferably varies between about 1 minute and 5 minutes depending upon the size of granule desired. For a granule of −6+ 16 mesh size (U.S. standard sieve) about 3 to 5 minutes is appropriate. For granules of −10+20 mesh size, 1–2 minutes may be sufficient.

Preferably the starting compound and binder combine to form a very fine granule in the cross spray described above, then fall to the bottom of the mixer and are gradually displaced forward as they grow, until they reach the desired granule size and fall out the open end. Depending upon the desired granule size, rate of introduction of starting components may be adjusted to cause the particles to progress at a rate which leaves them in the mixer for the desired time period. In accordance with the invention, no granulator is required between the mixing step and a subsequent drying step.

The binder and starting nutrient compound may also be introduced with a screw conveyer which has the additional advantage of helping control granule size. Because of the heat created by the ongoing exothermic reaction, drying begins also.

The binder is preferably a mixture of large and small polysaccharides which includes a high concentration of reducing sugars for participation in the reaction. In one preferred embodiment of the invention, the binder is a mixture consisting essentially of molasses and water, wherein the water is present in a concentration of 25% (by weight based on weight of the molasses and water combination), and more preferably 35% to 50% water (e.g., a mixture of 60% molasses and 40% water). The high concentration of water breaks down higher polysaccharides into both reducing monosaccharides and also aldehyde-containing disaccharides. Together with the reducible starting compound, these saccharides react to form carboxylates in accordance with the reactions set forth below. The resulting nutrient carboxylate is more available for uptake than the starting nutrient compounds (e.g., oxides). A typical product of the reaction is thus a carboxylate of a cationic nutrient having the formula:

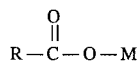

wherein M is the cationic nutrient and R is the saccharide residue, i.e., the remaining portion of the saccharide molecule other than its aldehyde group which has been converted to the carboxylate group.

One side product of the reaction, especially where dioxides such as $MnO_2$ are present in small amounts in the starting material, is an oxidized carbohydrate which further breaks down to yield carbon dioxide gas which can be trapped in the growing granule and which, during use, acts to disperse the active nutrients as the polysaccharide binder dissolves.

Without intending to be bound by theory, it is believed that amorphous polysaccharides break down to the aldehyde forms of disaccharides and monosaccharides and indeed to such sugars (carbohydrates) as d-glucose, d-mannose, d-fructose, etc.

Such reducing sugars have the general aldehyde structure:

With water and heat (energy), polysaccharides are hydrolyzed to disaccharides and then to monosaccharides. Plants do this with photosynthesis and actually secrete carboxyl groups to take up nutrients in ion exchange reactions.

Monosaccharides also undergo hydrolysis with water to convert from the aldehyde form to the carboxylate ion

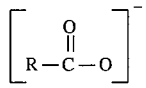

and to form carboxylic acid

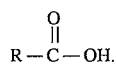

In the presence of some cations, notably Zn and Fe, even in the forms of ZnO, FeO and $Fe_2O_3$, the reaction potential is greater to form a zinc or iron carboxylate

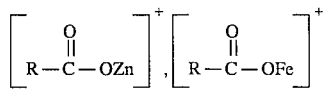

rather than the weak acid

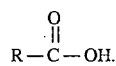

As can be seen from the above ion formations, the monosaccharide is actually oxidized by reducing the cation oxide. Indeed, this is to be expected since monosaccharides are reducing agents and act as such in the process.

Manganese (Mn) acts somewhat differently in that the x-ray diffraction patterns show that the $Mn^{++}$ ion "pops" in and out of the carboxylate structure.

It is known that the carbonyl group, i.e.,

is electron withdrawing and that in the carbonyl group, the carbon is partially positive and the oxygen is partially negative. It is also known that manganese has seven different valence states and goes up and down the scale at will Its most stable form is $Mn^{++++}$, although if kept in a reduced state, $Mn^{++}$ is stable.

It therefore follows that in the above process, the resultant manganese compound oscillates between

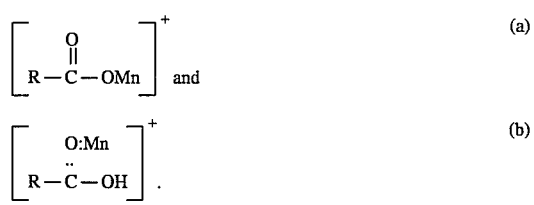

In either case, the total reaction can be represented as:

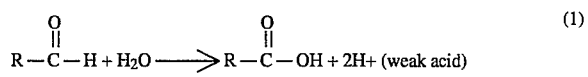

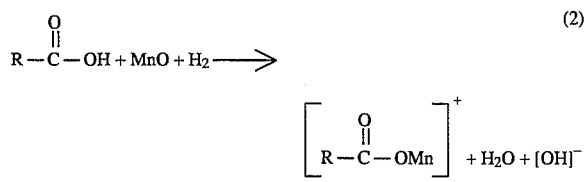

and similarly for zinc and iron.

In the case of (b) above, the reactions are:

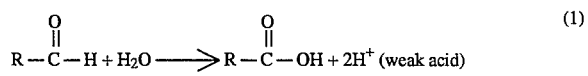

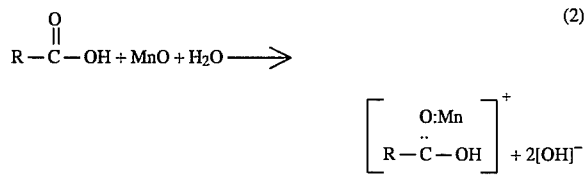

And indeed, the water dispersion of the granular nutrient materials tests mildly alkaline, as would be expected.

In order to achieve these carboxylates, it has now been found necessary to use excess reducing saccharides in the manufacturing process. This assures a more than ample supply of reducing sugars, carbonyl groups and carboxyl groups, not only to achieve the desired ionization but to keep the oxygen seeking cations in the reduced state.

Referring now to the drawings wherein like numerals indicate like elements, there is shown in FIG. 1 a mixing step 20 which may advantageously be carried out in a mixer as described above. The nutrient compounds (e.g. MnO) and the binder are mixed by cross-spraying them above the opening to the mixer. The mixture of the nutrient particles and the binder then enters the mixer through a raised end of the mixer.

The binder comprises a water soluble polysaccharide and/or a monosaccharide, such as the aldehyde forms of sugars, d-glucose (aldehyde form), d-mannose, d-fructose, osone, maltose, molasses, molasses extract, cane sugar extract, or beet sugar extract mixed with water. For example, 15 gallons of molasses (176 lbs. wet weight or 134 lbs. dry weight) with 10 gallons of water (83 lbs. $H_2O$) may be used. Molasses often contains at least 48% sugars (carbohydrates: monosaccharides, disaccharides and polysaccharides) with from 12% to 16% sucrose. A preferred binder is 60% molasses and 40% water (w/w).

The mixer is rotated so that the nutrient particles and the binder are mixed. The type of nutrient used and the size of the granules desired determine the processing time in the mixer. Broadly, longer times will produce coarser granules.

By way of illustration but without limitation of the scope of the invention, following are some examples of the process parameters of the invention.

Typical formulations for Mn, Zn and Fe are:

| Mn |
| --- |
| 1836 lbs. MnO, 43% Mn |
| 134 lbs. dry wt. binder (176 lbs. wet + water) |
| 30 lbs. final moisture (1.5%) |
| 2000 lbs. |
| Zinc, 36% Zn |
| 1714 lbs. Zinc Oxide, 42% Zn |
| 122 lbs. Lime (filler) |
| 134 lbs. Binder (dry wt. or 176 lbs. wet + water) |
| 30 lbs. Final Moisture (1.5%) |
| 2000 lbs. |
| Iron, 50% Fe |
| 1613 lbs. Iron Oxide, 62% Fe |
| 223 lbs. Lime (filler) |
| 134 lbs. Binder (dry wt. or 176 lbs. wet + water) |
| 30 lbs. Final Moisture (1.5%) |
| 2000 lbs. |

All above weights and measures are given in terms of per net ton of final product.

The output of mixer, in granular form, is fed to a dryer. (Drying step 22 is carried out in the dryer.) Any dryer well known in the art such as a belt dryer, a tumble dryer or a rotary dryer, may be used. A preferred drying unit allows progression of the granules from a "cold" end to a hot end thereof. (It should be noted that even the cold end is well above ambient temperature.) Such a drying unit may include a heat source at its hot end and a counter current air flow moving in a direction opposite to the motion of the granules (i.e., away from the hot end and toward the cold end). The air naturally cools as it travels toward the cold end and away from the heat source. The temperature range at the hot end depends upon the type of dryer and the desired drying time, preferably from 180° F.–350° F. The higher temperatures have been found preferable.

The moisture content of the material being fed to the dryer is preferably between 5% and 20% depending upon the desired size of the final granules and their desired porosity. Typical granules have a dryer input moisture content of 10% to 12% and a dryer output moisture content of 1% to 5%.

From drying step 22, the material is fed to screening step 24. At this step, where granules (−8 +20 for example) are to be shipped, all granules larger than 8 mesh are fed to grinding step 28 where any standard grinder is used to pulverize the oversize granules. All granules smaller than mesh 20 (considered to be fines for this purpose) are also screened out. Both the fines and the pulverized coarse granules are recycled back to the mixer and reprocessed by the method of the invention.

The proper size granules are preferably then cured in the curing step 26 for a sufficient time period to permit substantial termination of exothermic carboxylate-forming reactions. Preferably the product is cured until it has returned to ambient temperature, and preferably for at least 12 to 24 hours thereafter. Subsequently, the product may be fed to a packaging step as required, or formulated as a component into other nutrient-containing products.

Magnesium Carboxylate as a Nutrient Pesticide

I Chemistry

A. Starting material (raw material)
Calcined magnesite (MgO)
1. There are two types of MgO, "dead burned" and lightly calcined; the difference is shown below:

a. $MgCO_3 \xrightarrow{\Delta} MgO \; xH_2O \; yCO_2$ (Intense) where x and y=o
This type is unreactive and stable; it is excellent for firebrick and founding linings but not suitable as a plant or animal nutrient since it is non-reactive and unavailable.

b. $MgCO_3 \xrightarrow{\Delta} MgO \; xH_2O \; yCO_2$ where x and y are >1
This lightly calcined magnetite (reactive magnesium oxide) is available as a nutrient to plants and animals, but not suitable for firebrick or foundry lining applications because upon heating to 1000° C., it gives off molecular $H_2O$ and $CO_2$, thereby destroying the firebrick and/or the foundry lining.

B. Reactions of lightly calcined MgO $MgO + H_2O \rightarrow MgO \; H_2O$    1.

This water is "molecular water" and increases the reactivity of MgO all colloidal suspension in water $MgO + 2H_2O \rightarrow Mg(OH)_2$    2.

$MgO + NH_4SO_4 \rightarrow MgSO_4 \cdot OH + NH_3 \uparrow$    3.

C. Reducing sugars—Monosaccharides; Making Magnesium Carboxylate

Monosaccharides undergo hydrolysis with water to convert to the aldehyde form to the carboxylate ion $$\left[ \begin{array}{c} O \\ \| \\ R-C-O \end{array} \right]^-$$

and to form carboxylic acid $$\begin{array}{c} O \\ \| \\ R-C-OH. \end{array}$$

In the presence of magnesium and/or magnesium oxide (MgO $CO_2$ $H_2O$), the reaction potential is to form the magnesium carboxylate ion, i.e., $$\left[ \begin{array}{c} O \\ \| \\ R-C-O \end{array} \right]^+$$

Mg and Carboxylic acid.

$$\begin{array}{c} O \\ \| \\ R-C-OH. \end{array}$$

The full reaction is:

$MgO \; CO_2 \; H_2O + H_2O > Mg(OH)_2 + H_2CO_3$ $$R-\overset{O}{\underset{\|}{C}}-OH + Mg(OH)_2 + H_2CO_3 > \left[ R-\overset{O}{\underset{\|}{C}}-O \; Mg \right]^+ +$$

$$[OH]^- + H_2O + CO_2$$

$$\left[ R-\overset{O}{\underset{\|}{C}}-O \; Mg \right]^+ + [OH]^- + H_2O + CO_2 \; >$$

$$MgO \; R-\overset{O}{\underset{\|}{C}}-OH + H_2CO_3$$

Then the carbonic acid, when not under pressure, returns to $CO_2$ plus $H_2O$, i.e., $H_2CO_3 \rightarrow CO_2\uparrow + H_2O$. The $Co_2$ released bursts the granule apart, into fine particles of 44 microns each, since the raw material was ground to 44 micron size before processing it into magnesium carboxylate.

D. Choice of Magnesium Compound as a Natural Nutrient Pesticide

When magnesium oxide (lightly calcined) is placed in water, if it is in finely divided powdered from (i.e., 44 micron particle size), it, too, will have the reaction, $MgO \; CO_2 \; H_2O + H_2O \rightarrow Mg(OH)_2 + H_2CO_3$ and $H_2CO_3 \rightarrow H_2O + CO_2$ If the MgO is a coarse granular, −6+16 mesh, with time, it will undergo the same reaction. However, the time necessary for water to break down the large −6+16 mesh granules varies between one and two years in the soil. Hence, the magnesium carboxylate is preferred since it disperses with water in a matter of minutes. Therefore, magnesium carboxylate is the preferred choice for immediate pesticidal reaction. Furthermore, the magnesium carboxylate contains monosaccharides (reducing sugars) as a bait. However, the invention discloses a choice of two (2) products which can be used:

PRODUCT A: Magnesium Carboxylate (or Sucrate) as described above.

PRODUCT B: A physical blend of coarse granules, −6+16 mesh, lightly calcined MgO and Magnesium Carboxylate (Sucrate) in a 1:1 ratio. This product will provide immediate action plus a long term pesticide action.

It should be explained that for application of this pesticide, the product can be applied in several ways, all of which require a granule of the mesh sizes, −6+16 mesh (U.S. Standard Sieve or Tyler) or −10+20 mesh (U.S. Standard Sieve or Tyler).

E. Methods of Application

1. Coarse granule (−6+16 mesh) dispersing granular magnesium carboxylate (sucrate) is applied as part of a mixed fertilizer so long as the fertilizer is broadcast or banded. In this manner, the plant not only receives magnesium as a nutrient, but is shielded against insecticidal damage.

The product must be coarse granular, −6+16 mesh, so as not to segregate from the other bulk blended fertilizer ingredients, or −10+20 mesh for turf application.

Applying a nutrient which is also a pesticide saves an extra pesticidal application.

2. Coarse granule (−6+16 mesh) or fine granule (−10+20 mesh) dispersing granular magnesium sucrate can be applied as a post emergence solid material by the use of a "whirlybird" or as an aerial application, as direct application by itself.

3. Since the granules disperse readily in water, the dispersing granular magnesium sucrate can be added to water. With agitation, within minutes a suspension of 44 micron particles of magnesium sucrate is created. This suspension is then sprayed as a post emergence spray on the crop or plants. Once the spray dries, the magnesium sucrate particles have their own spray adjuvant (monosaccharide) which sticks the particles to the leaves of the plant. Thus, the feeding suppressant is in place.

4. For the control of fire ants on lawns, the product can be supplied as a −10+20 mesh particle packed in a large "salt shaker." By shaking the particles on top of the fire ant hills, the fire ants disappear within a day. The same manner of application will work for mole crickets on lawns and/or golf courses. For the latter, standard dry fertilizer application methods are used.

F. Rates of Application

The equivalent of from 40 lbs. to 90 lbs. of 100% elemental Mg should be applied per acre for the control of the aforementioned insects, depending upon the particular insect. The dispersing granular Magnesium sucrate analyzes from 42% to 45% elemental Mg. Therefore, one should apply from 100 to 200 lbs. of the product per acre four times per year, more or less depending upon the insect to be controlled. However, for lawn application and for insecticidal action on fire ants, the application should be more like 1 to 1.5 ounces per square foot. By making the product more dilute, it could be applied in larger amounts to get better coverage.

Agronomic toxicity from magnesium is virtually nonexistent and unheard of. In fact, magnesium is the nucleus of the chlorophyll molecule and usually, the more magnesium, the better.

The methods of application are particularly novel because powdered magnesium oxide, particularly in the range of 44 micron particle size, is difficult, if not impossible to apply in the dry form because of dusting, inhalation of dust and air pollution. It is also difficult, if not impossible to immerse such a powder in water (like trying to stir talcum powder into a glass of water) without a wetting agent. The dispersing granules of magnesium sucrate drop easily into water and with agitation produce a suspension without the addition of a wetting agent.

Furthermore, if the insecticide is applied in the mixed fertilizer, the separate application of an insecticide (such as Diazinon) becomes unnecessary, not only saving the price of the chemical itself (Diazinon), but also the cost of the extra application. Even the spraying of a slurry of dispersed granular magnesium sucrate will act as a nutrient as well as an insecticide since plants can take up nutrients through the leaf surface.

G. How the Magnesium Products Work

Once the dispersing granular magnesium carboxylate (sucrate) breaks down into 44 micron particles (very shortly after contacting water or soil moisture) or the coarse granular magnesium oxide breaks down into small particles (between one and two years after application to the soil or as a post emergence to the crop or turf), the products affect the insects in three ways:

a. When the insects come into the physical contact with the small particles of the magnesium product, the external placenta of the insect is irritated, causing rapid dehydration and death;

b. Once the finely divided particles of the magnesium product are ingested by the insect, rapid dehydration and death occur due to the fact that magnesium is a laxative, a cathartic and a diuretic;

c. Learning the results of (b.), insects shy away from the magnesium products, do not feed, and die of starvation. Thus, the magnesium products become a feeding suppressant.

H. Evidence of Action and Effectiveness

1. Tests showed that Magnesium Carboxylate (Sucrate) caused above 86% mortality of Fall Army Worm larvae over a 6-week period and finely divided (powdered) MgO caused about a 67% mortality rate over the same period, when both were included in the feed.

2. Moreover, Magnesium Carboxylate (Sucrate) granules dispersed in water showed above a 50% increase in Fall Army Worm mortality over a 96-hour (4-day) period, demonstrating the faster action of the compound.

3. Further tests demonstrated that the higher the elemental Mg concentration of the product, the greater effectiveness of the compound as an insecticide.

4. Tests upon corn showed that finely divided MgO reduced Fall Army Worm damage by 90% as a post emergence application.

5. Similar tests performed on cabbage showed that finely divided (powdered) MgO reduced damage by 24% within nine days and another 14% within 19 days, both from cabbage loopers and diamondback moths.

These same field tests showed a reduction of insect counts (diamondback moths and cabbage loopers) of from 25% to 67% within 24 days.

6. Application of MgO of −6+16 mesh granular particle size (from 1 to 3.35 mm) showed that after a one to two-year application, Fall army worms disappeared from pastures, and pecudos (long black-beaked beetles) which feed upon and nest in the roots of bananas and plantain trees also disappeared.

7. Application of −6+16 mesh coarse granular dispersing magnesium carboxylate (sucrate), both as an ingredient in bulk blended fertilizer and as a separate direct application, on the 13th hole of an 18-hole golf course badly infested with mole crickets and chinch bugs showed only one mole cricket and no chinch bugs on the 13th hole after 3 weeks, whereas the balance of the golf course was still infected after treatments with other insecticides. Moreover, on another golf course (one hole/fairway) treatment at the rate of 200 lbs./acre of magnesium carboxylate (sucrate) demonstrated complete control of mole crickets during a six-week period without other chemical pesticidal treatment while the balance of the golf course was treated with other chemical pesticides and continued to experience re-infestations of mole crickets during the same 6-week period.

Additionally, the turf on the magnesium carboxylate (sucrate) hole was healthier and greener than the balance of the golf course.

8. Similar applications of dispersing granular magnesium carboxylate (sucrate) on residential lawns infested with fire ants cleared the lawns from fire ants within one week.

9. Another direct and separate application of dispersing granular magnesium carboxylate (sucrate) on soil surrounding citrus trees in a citrus grove showed 100% eradication of nematodes after 3 weeks.

I. Insects Affected

Nematodes, Fall Army Worms, Cabbage Loopers, Diamondback Moths, Cabbage Worm, Corn Ear Worm, Corn Borer, Corn Worm, Squash Vine Borer, Sweet Potato Weevil, Tuberworm, Webbworm, Wireworm, Pecudos (long-beaked black beetle), Chinch Bugs, Mole Crickets and Phylloxera are controlled by the compounds employed in the invention. While tests have been extensive, it has not been possible to test the pesticidal action on every insect known. Therefore, the aforementioned list of insects is not meant to be limiting to those names, but only inclusive.

J. Advantage of Magnesium Carboxylate (Sucrate) In A Mixed, Bulk Blended Fertilizer As A Nutrient Pesticide MgO is more agronomically available to the plant than Epsom Salt, $MgSO_4$, Kieserite or magnesium potassium sulfate. However, it is not as quickly available as the aforementioned water soluble Mg substances.

Magnesium Carboxylate (Sucrate) is more readily available to the plant than MgO and resists leaching and run-off.

Also, MgO, when blended into a fertilizer containing $NH_4SO_4$, $NH_4NO_3$, urea or other nitrogen salts, releases $N_2$ in the form of ammonia, the odor of which is highly objectionable. Dispersing granular Magnesium Carboxylate (Sucrate) significantly reduces the release of $NH_3$ since the complex, large molecule does not quickly enter into the chemical reaction which releases the ammonia.

Hence, Magnesium Carboxylate (Sucrate) is highly agronomically available, resists leaching and run-off and avoids the objectionable $NH_3$ release and acts as an extremely effective pesticide and is very environmentally responsible.

K. Comparison with Soluble Magnesium Forms

Water soluble forms of Mg ($MgSO_4$ Epsom Salts, Kieserite, Potassium Magnesium Sulfate, etc.) do not form fine solid particles which irritate the external placenta of insects to dehydrate them and they do not furnish the high Mg uptake by the plant in a high enough concentration to cause dehydration by ingestion or to suppress insect feeding.

L. Choice of Product

The two products preferred herein are:

1. Magnesium Carboxylate (Sucrate) in a water or soil moisture dispersing form as a −6+16 mesh dispersing granule or a −10+20 mesh dispersing granule size, either directly and separately applied or applied in a bulk blended, dry mixed fertilizer.

2. A physical blend of a 50:50 ratio of coarse granular, −6+16 mesh, lightly calcined MgO with a −6+16 mesh, dispersing granular Magnesium Carboxylate (Sucrate).

3. The choice of either depends upon:
   a. Avoidance of objectionable $NH_3$ release;
   b. Speed of Effectiveness;
   c. Durability of Effectiveness;
   c. Non-dusting Properties (Magnesium Carboxylate [Sucrate] is significantly less dusty.)

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for controlling soil insects, the step comprising applying to soil containing such insects, an amount sufficient to control the growth of the insects of a soil dispersible and water dispersible granular nutrient consisting of a crystallized saccharide binder having a metal carboxylate selected from the group consisting of magnesium carboxylate and boron carboxylate embedded therein.

2. The method according to claim 1 wherein the granular nutrient applied contains a plurality of fine particles of nutrient carboxylate, an outer coating of the binder binding the fine particles into a unitary granule, and entrapped gas in the unitary granule.

3. The method according to claim 1 wherein the amount of granular nutrient applied is about from 100 to 200 pounds per acre.

4. The method according to claim 1 wherein the metal carboxylate applied is magnesium carboxylate.

5. The method according to claim 4 wherein the magnesium carboxylate contains a monosaccharide.

6. The method according to claim 1 wherein the granular nutrient is applied in a physical blend of coarse granules of about −6+16 mesh, lightly calcined magnesium oxide to magnesium carboxylate in about a 1:1 ratio.

7. The method according to claim 1 wherein the granular nutrient is applied at a mesh size of −6+16 mesh to −10+20 mesh.

8. The method according to claim 1 wherein the granular nutrient is applied to fire ants in about a −10+20 mesh particle size with the application made by shaking the particles on top of a fire ant hill.

9. The method according to claim 1 wherein the granular nutrient is applied to lawns containing fire ants at a rate of 1 to 1.5 ounces per square foot.

10. The method according to claim 9 wherein the granular nutrient is magnesium carboxylate.

* * * * *